United States Patent [19]

Freedman et al.

[11] Patent Number: 4,766,212

[45] Date of Patent: Aug. 23, 1988

[54] 2H-[1]BENZOXEPINO[5,4-b]-1,4-OXAZINE DERIVATIVES

[75] Inventors: Jules Freedman; Richard C. Dage, both of Cincinnati, Ohio

[73] Assignee: Merrell Dow Pharmaceuticals Inc., Cincinnati, Ohio

[21] Appl. No.: 114,475

[22] Filed: Oct. 29, 1987

Related U.S. Application Data

[63] Continuation-in-part of Ser. No. 45,918, May 4, 1987, abandoned, which is a continuation of Ser. No. 811,591, Dec. 20, 1985, abandoned, which is a continuation-in-part of Ser. No. 748,700, Jun. 25, 1985, abandoned, and Ser. No. 748,701, Jun. 25, 1985, abandoned, said Ser. No. 748,700, is a continuation of Ser. No. 562,759, Dec. 21, 1983, abandoned, which is a continuation-in-part of Ser. No. 466,407, Feb. 15, 1983, abandoned, said Ser. No. 748,701, is a continuation of Ser. No. 562,757, Dec. 21, 1983, abandoned, which is a continuation-in-part of Ser. No. 466,442, Feb. 15, 1983, abandoned.

[51] Int. Cl.$^4$ .......................................... C07D 498/04
[52] U.S. Cl. ........................................ 544/101; 544/99
[58] Field of Search ................ 544/99, 101; 514/227, 514/237, 239

[56] References Cited

U.S. PATENT DOCUMENTS 4,318,910  3/1982  Nedelec et al. .................. 544/99 X
4,349,548  9/1982  Jones ............................. 544/101 X

FOREIGN PATENT DOCUMENTS 116373  8/1984  European Pat. Off. .
116372  8/1984  European Pat. Off. .

*Primary Examiner*—Richard L. Raymond
*Attorney, Agent, or Firm*—John J. Kolano

[57] ABSTRACT

Derivatives of 2H-[1]benzoxepino[5,4-b]-1,4-oxazine, such as trans-3,4,4a,5,6,11b-hexahydro-10-methoxy-2H-[1]benzoxepino[5,4-b]-1,4-oxazine, are prepared by acylating a trans-4-amino-2,3,4,5-tetrahydro-1-benzoxepin-5-ol, cyclizing the resulting chloroacetamido alcohol, reducing the 1,4-oxazine-3(4H)-one so obtained, acylating the resulting 2H-[1]-benzoxepino[5,4-b]-1,4-oxazine, and reducing the N-acryl-2H-[1]benzoxepino[5,4-b]-1,4-oxazine so obtained. The novel compounds disclosed herein possess useful antihypertensive properties.

9 Claims, No Drawings

2H-[1]BENZOXEPINO[5,4-b]-1,4-OXAZINE DERIVATIVES

CROSS-REFERENCE TO RELATED APPLICATION

This application is a continuation-in-part of application Ser. No. 45,918, filed May 4, 1987 (now abandoned) which in turn is a continuation of application Ser. No. 811,591, filed Dec. 20, 1985 (now abandoned), which in turn is a continuation-in-part application of applications Ser. Nos. 748,700 and 748,701, each filed on June 25, 1985 (both now abandoned); application Ser. No. 748,700 being a continuation of application Ser. No. 562,759, filed Dec. 21, 1983 (now abandoned) which in turn was a continuation-in-part of application Ser. No. 466,407, filed Feb. 15, 1983 (now abandoned) and application Ser. No. 748,701 being a continuation of Ser. No. 562,757, filed Dec. 21, 1983, (now abandoned) which in turn was a continuation-in-part of Ser. No. 466,442 filed Feb. 15, 1983 (now abandoned).

SUMMARY OF THE INVENTION

This invention relates to 2H-[1]benzoxepino[5,4-b]-1,4-oxazine derivatives which may be substituted at the phenyl ring or at the amine nitrogen atom. More particularly, this invention relates to the cis- and trans-3,4,4a,5,6,11b-hexahydro-2H-[1]benzoxepino[5,4-b]-1,4-oxazine derivatives having the following general formula

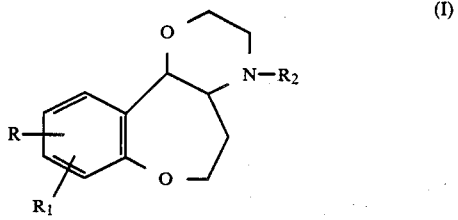

wherein R and $R_1$ are each hydrogen, hydroxy, lower alkyl, halogen, $CF_3$, $NO_2$ or $NH_2$, loweralkoxy, or when taken together are methylenedioxy, $R_2$ is selected from the group consisting of hydrogen, loweralkyl, phenyl(loweralkyl), (loweralkoxy)($C_{2-4}$ loweralkyl), cyclopropylmethyl, 2-furanylmethyl and $R_3R_4N(C_{2-4}$ loweralkyl) wherein $R_3$ and $R_4$ are each hydrogen or loweralkyl; and the pharmaceutical acceptable salts thereof. These derivatives possess useful analgesic and muscle relaxant activity. Some of the compounds also possess useful antihypertensive activity. Further, this invention relates to useful processes for the preparation and use of the compounds of formula I.

One embodiment of the present invention relates to those compounds of formula I wherein R and $R_1$ are each hydrogen, hydroxy or loweralkoxy; or R and $R_1$ are each hydrogen, loweralkyl, fluoro or chloro; or R and $R_1$ taken together are methylenedioxy; $R_2$ is selected from the group consisting of hydrogen, loweralkyl, phenyl(loweralkyl), (loweralkoxy)($C_{2-4}$ loweralkyl), cyclopropylmethyl, 2-furanylmethyl and $R_3R_4N$-($C_{2-4}$ loweralkyl) wherein $R_3$ and $R_4$ are each hydrogen or lower alkyl; and the pharmaceutically acceptable salts thereof.

The structural formula as shown above encompasses both the cis and trans forms of the compounds involved. The terms cis and trans as used above indicates the geometry of the fusion of the oxepine and 1,4-oxazine rings. For each of these geometric isomers, two enantiomers are possible and the present invention encompasses these individual enantiomers and also racemic mixtures of these enantiomers.

As defined for the compounds of formula I, the benzenoid moiety of the depicted benzoxepino moiety may bear one or two of the substituents for R and $R_1$. When so substituted, the substituents may be located at any one of the four positions available, i.e., at position 8-, 9-, 10- or 11-. When R and $R_1$ are taken together as methylenedioxy, the R and $R_1$ must be situated on adjacent positions of the benzenoid ring.

The term "lower" as it defines such radicals as alkyl or alkoxy is meant to include those radicals having 1 to 4 (or, where specifically indicated, 2 to 4) carbon atoms such as may be illustrated by lower alkyl as for example, methyl, ethyl, propyl, isopropyl, butyl, isobutyl and t-butyl. Preferred substituents are methyl and ethyl, methoxy and ethoxy, benzyl, phenethyl. Preferred (loweralkoxy)($C_{2-4}$ loweralkyl) radicals are methoxyethyl and ethoxypropyl. Preferred $R_3R_4N$-($C_{2-4}$ loweralkyl) radicals are aminoethyl and dimethylaminoethyl. Preferred halogens are chloro and fluoro.

In the term $R_3R_4N$-($C_{2-4}$ loweralkyl) as used herein, the nitrogen can be either a primary, secondary or tertiary amine. In addition, the nitrogen is separated from the point of attachment to the oxazine ring by at least two carbon atoms. Illustrative of such groups are the 2-aminoethyl, 2-aminopropyl, 2-(ethylamino)ethyl, 2-(dimethylamino)ethyl or 3-[N-methyl(propylamino)]-propyl groups. Similarly, in the term (loweralkoxy)(-$C_{2-4}$ loweralkyl), the oxygen of the loweralkoxy group is separated from the point of attachment to the oxazine ring by at least two carbon atoms.

The expression pharmaceutically acceptable salts refer to those non-toxic organic or inorganic acid addition salts which are equivalent to the above amines for the purposes of this invention. Illustrative inorganic acids which form suitable salts are hydrochloric, hydrobromic, sulfuric and phosphoric acid as well as acid metal salts such as sodium monohydrogen orthophosphate and potassium hydrogen sulfate. Illustrative organic acids which form suitable salts include the mono-, di- and tri-carboxylic acids, for example, acetic, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Such salts can exist in either a hydrated or a substantially anhydrous form.

Illustrative compounds encompassed by the present invention are the cis and trans forms of:
10-ethoxy-3,4,4a,5,5,11b-hexahydro-4-propyl-2H-[1]benzoxepino[5,4-b]-1,4-oxazine;
8-butoxy-9-ethoxy-4-(3-ethoxypropyl)-3,4,4a,5,6,11b-hexahydro-2H-[1]benzoxepino[5,4-b]-1,4-oxazine;
3,4,4a,5,6,11b-hexahydro-9-methoxy-4-phenethyl-10-propoxy-2H-[1]benzoxepino[5,4-b]-1,4-oxazine;
4-(2-furanylmethyl)-3,4,4a,5,6,11b-hexahydro-9-hydroxy-2H-[1]benzoxepino[5,4-b]-1,4-oxazine;
4-dimethylaminoethyl-3,4,4a,5,6,11b-hexahydro-9-hydroxy-8-methoxy-2H-[1]benzoxepino[5,4-b]-1,4-oxazine;
4-cyclopropylmethyl-9,10-dihydroxy-3,4,4a,5,6,11b-hexahydro-2H-[1]benzoxepino[5,4-b]-1,4-oxazine;

3,4,4a,5,6,11b-hexahydro-8,9-methylenedioxy-4-(2-methylpropyl)-2H-[1]benzoxepino[5,4-b]-1,4-oxazine;
10-ethyl-3,4,4a,5,6,11b-hexahydro-4-propyl-2H-[1]benzoxepino[5,4-b]-1,4-oxazine;
8-butyl-9-fluoro-4-(3-ethoxypropyl)-3,4,4a,5,6,11b-hexahydro-2H-[1]benzoxepino[5,4-b]-1,4-oxazine;
3,4,4a,5,6,11b-hexahydro-9-(2-methylpropyl)-4-phenethyl-10-propyl-2H-[1]benzoxepino[5,4-b]-1,4-oxazine;
4-(2-furanylmethyl)-3,4,4a,5,6,11b-hexahydro-9-propyl-2H-[1]benzoxepino[5,4-b]-1,4-oxazine;
4-dimethylaminoethyl-3,4,4a,5,6,11b-hexahydro-8,9-diethyl-2H-[1]benzoxepino[5,4-b]-1,4-oxazine;
4-cyclopropylmethyl-3,4,4a,5,6,11b-hexahydro-2H-[1]benzoxepino[5,4-b]-1,4-oxazine;
3,4,4a,5,6,11b-hexahydro-8,9-dichloro-4-(2-methylpropyl)-2H-[1]benzoxepino[5,4-b]-1,4-oxazine;
3,4,4a,5,6,11b-hexahydro-4-methyl-2H-[1]benzoxepino[5,4-b]-1,4-oxazine;
3,4,4a,5,6,11b-hexahydro-4-ethyl-2H-[1]benzoxepino[5,4-b]-1,4-oxazine;
3,4,4a,5,6,11b-hexahydro-8-methoxy-2H-[1]benzoxepino[5,4-b]-1,4-oxazine;
10-fluoro-3,4,4a,5,6,11b-hexahydro-2H-[1]benzoxepino[5,4-b]-1,4-oxazine;
10-fluoro-3,4,4a,5,6,11b-hexahydro-4-methyl-2H-[1]benzoxepino[5,4-b]-1,4-oxazine;
9-fluoro-3,4,4a,5,6,11b-hexahydro-4-methyl-2H-[1]benzoxepino[5,4-b]-1,4-oxazine;
9-fluoro-3,4,4a,5,6,11b-hexahydro-2H-[1]benzoxepino[5,4-b]-1,4-oxazine;
although the trans form compounds are preferred.

The novel 3,4,4a,5,6,11b-hexahydro-2H-[1]-benzoxepino[5,4-b]-1,4-oxazines of formula I can be readily prepared as illustrated in the following reaction scheme:

Thus, a substituted 4-amino-2,3,4,5-tetrahydro-1-benzoxepin-5-ol (II) can be acylated with chloroacetyl chloride in the presence of a trialkylamine, such as triethylamine to yield the corresponding substituted 2'-chloro-N-(2,3,4,5-tetrahydro-5-hydroxy-1-benzoxepin-4-yl)acetamide (III). The acylation can be conducted in an inert, halogenated solvent such as chloroform or methylene chloride at a temperature ranging from about 10° to about 30° C.

The chloroacetamido alcohol (III) can be cyclized with strong alkali in an aqueous alcohol solution. More particularly, cyclization can occur using a concentrated solution (50%) of sodium hydroxide in isopropanol or aqueous isopropanol at room temperature for a period of from 8 to 24 hours.

The substituted 4a, 5,6,11b-tetrahydro-2H-[1]-benzoxepino[5,4-b]-1,4-oxazine-3(4H)-one (IV) so obtained is reduced using a hydride reagent or diborane in an inert organic solvent. More particularly, lithium aluminum hydride can be favorably employed in a refluxing solvent, such as tetrahydrofuran or diethyl ether for a period of from about 3 to 12 hours. Where the symbol $R_2$ represents hydrogen in formula I above, the substituted 3,4,4a,5,6,11b-hexahydro-2H-[1]benzoxepino[5,4-b]-1,4-oxazines (V) are obtained.

Alternatively, where the symbol $R_2$ is other than hydrogen in formula I above the resulting substituted 3,4,4a,5,6,11b-hexahydro-2H-[1]-benzoxepino-[5,4-b]-1,4-oxazines (V) are conveniently acylated with an acid chloride or an acid anhydride in the presence of a trialkylamine. Acylation can again be conducted in the presence of an inert halogenated solvent such as chloroform or methylene chloride to provide the corresponding substituted-N-acyl-3,4,4a,5,6,11b-hexahydro-2H-[1]benzoxepino[5,4-b]-1,4-oxazines (VI), wherein $R_2'$ is the same as $R_2$ except that it contains one less carbon atom (i.e., one less methylene group).

Reduction of these N-acyl-2H-[1]benzoxepino[5,4-b]-1,4-oxazines (VI) using a hydride or diborane reagent provides the desired 3,4,4a,5,6,11b-hexahydro-2H-[1]benzoxepino[5,4-b]-1,4-oxazines (VII), wherein the symbol $R_2'$ is defined as above. More particularly, lithium aluminum hydride can be favorably employed in an inert, refluxing solvent, such as tetrahydrofuran or diethyl ether for a period of from about 3 to 12 hours.

Reaction Scheme A:

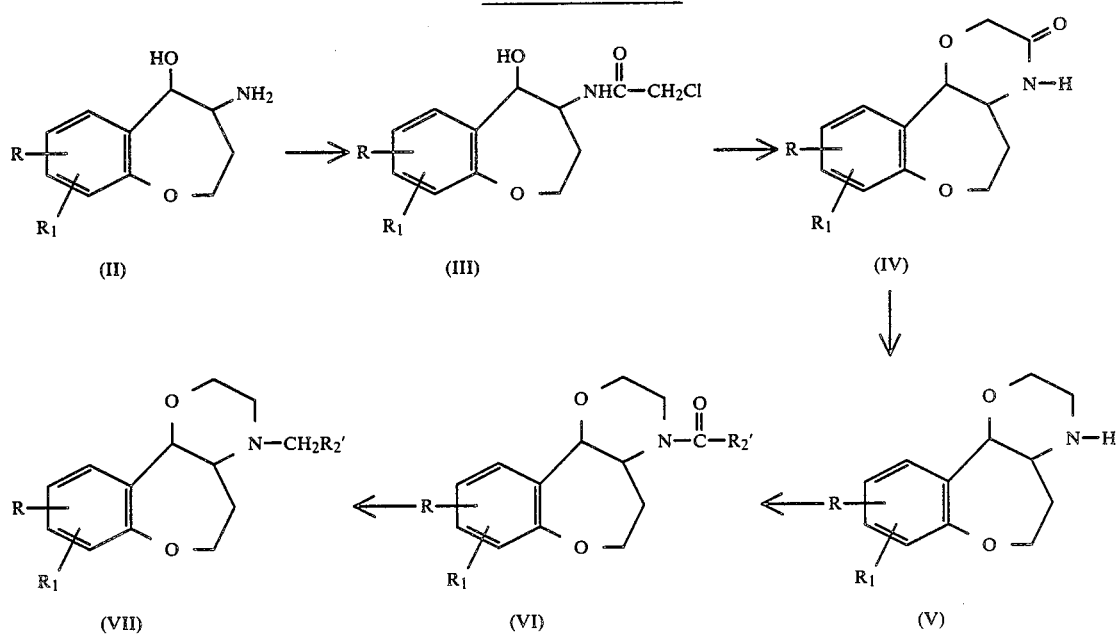

Alternatively, where the symbol $R_2$ in formula I represents a methyl group, it may be preferable to reduce the N-carboxylic acid ester in lieu of the N-acyl derivative in the last step of the reaction sequence. Thus, the substituted 3,4,4a,5,6,11b-hexahydro-2H-[1]benzoxepino[5,4-b]-1,4-oxazines (V) can be reacted within alkyl chloroformate in the presence of a trialkylamine and a solvent such as chloroform or methylene chloride to provide the corresponding substituted 3,4,4a,5,6,11b-hexahydro-4-carboalkoxy-2H-[1]benzoxepino[5,4-b]-1,4-oxazine derivatives (VIII) having the general formula

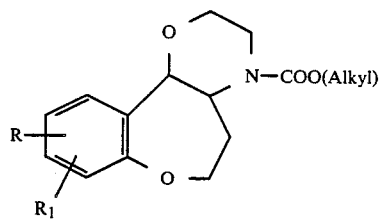

(VIII)

Reduction of this 4-carboalkoxy derivative with a hydride or diborane reagent, using essentially the same procedure as for the reduction of the N-acyl-3,4,4a,5,6,11b-hexahydro-2H-[1]benzoxepino[5,4-b]-1,4-oxazine (VI), provides the desired 4-methyl derivative.

It is to be noted that the intermediate 4-amino-2,3,4,5-tetrahydrobenzoxepin-5-ol compounds (II) may exist in either their cis or trans geometric isomeric forms, each of which are enantiomeric mixtures which may be separated into individual enantiomers by methods known in the art such as by the formation of diastereomeric salts. Alternatively, each enantiomer can be synthesized from an optically pure starting material. All such isomers are embraced herein although throughout this specification it is preferred, from an end-use application of the compounds of this invention (I), to utilize the trans isomers.

The substituted 4-amino-2,3,4,5-tetrahydro-1-benzoxepin-5-ol compounds (II) useful as starting materials are either known compounds or compounds that can be readily prepared from known phenols or substituted phenols in accordance with the following reaction scheme:

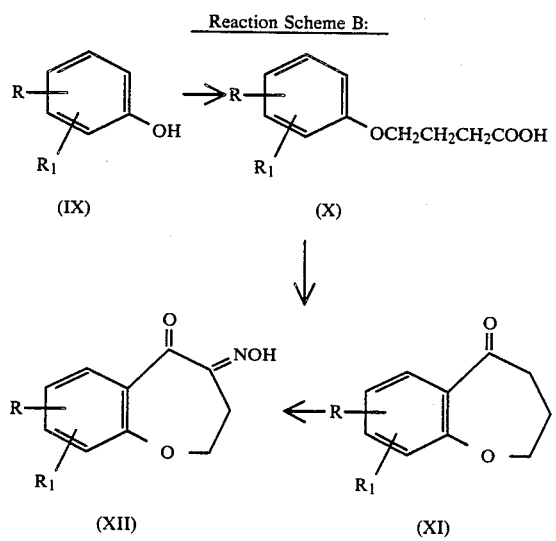

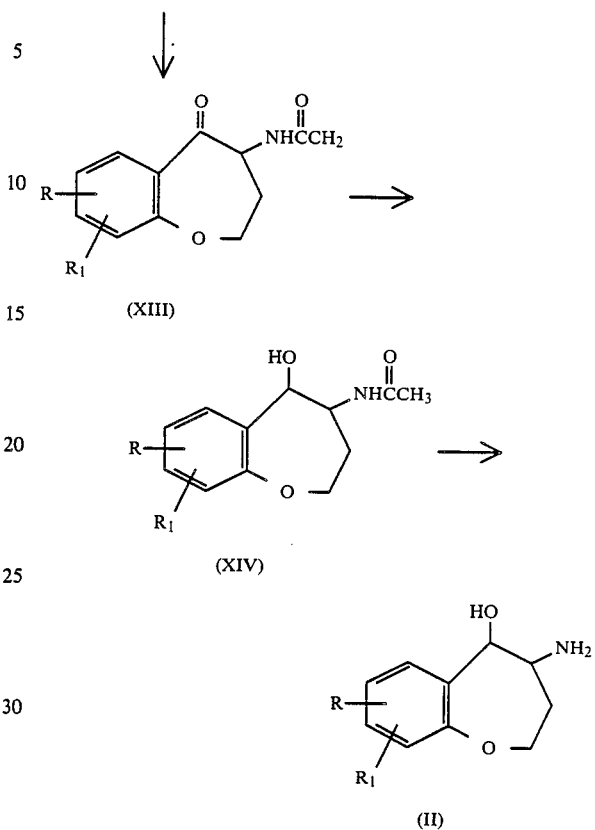

Thus, phenol or a substituted phenol (IX) can be converted to the corresponding phenyloxybutyric acids (X) by heating the corresponding sodium phenolate with a slight excess of butyrolactone at a temperature of about 150°–155° C. These phenyloxybutyric acids can be cyclized by heating with polyphosphoric acid at temperatures from about 55° to 100° C. to yield the corresponding 3,4-dihydro-1-benzoxepin-5(2H)-ones (XI). The 3,4-dihydro-1-benzoxepin-5(2H)-ones so obtained (XI) can be dissolved in a solution of sodium ethoxide in ethanol and treated with isoamyl nitrite at ice-bath temperatures to form the 2,3-dihydro-1-benzoxepin-4,5-dione-4 oximes (XII).

The oximino ketones (XII) obtained in this manner can be reduced with zinc dust in an acetic acid/acetic anhydride mixture at temperatures of about 50°–65° C. to form the corresponding 3,4-dihydro-4-acetamido-1-benzoxepin-5-ones (XIII). Further reduction of these compounds by means of sodium borohydride in ethanol at temperatures ranging from about 10° to 30° C. results in the formation of a mixture of the corresponding cis- and trans-2,3,4,5-tetrahydro-4-acetamido-1-benzoxepin-5-ols (XIV). Recrystallization of this mixture from a solvent such as ethyl acetate or acetonitrile results in the isolation of the individual isomers, with the trans isomer generally being less soluble than the cis. Hydrolysis of these isomers (XIV) by means of a refluxing solution of aqueous sodium hydroxide in ethanol provides the desired cis or trans substituted 4-amino-2,3,4,5-tetrahydro-1-benzoxepin-5-ols (II), useful as starting materials for the preparation of the compounds of the present invention.

The following examples are provided to further illustrate the present invention but should not by construed as limiting the invention in any way.

EXAMPLE 1

Trans-3,4,4a,5,6,11b-Hexahydro-10-methoxy-2H-[1]benzoxepino[5,4-b]-1,4-oxazine Hydrochloride A stirred suspension of 54 g (0.22 m) of 4-acetamido-7-methoxy-3,4-dihydrobenzoxepin-5(2H)-one in 600 ml of ethanol is cooled in an ice bath and 11 g of sodium borohydride is added (portionwise) under argon and the reaction mixture is stirred for an additional three hours. The solvent is evaporated, in vacuo, and the residue dissolved in one liter of water. The aqueous mixture is extracted with EtOAc (3×200 ml) and the combined extracts water washed (2×150 ml), dried (MgSO$_4$), filtered and evaporated to dryness in vacuo to yield a yellow solid which is digested with 1 liter EtOAc with extended heating. The remaining undissolved material is removed by filtration to yield 21.25 g of trans-4-amido-7-methoxy-2,3,4,5-tetrahydrobenzoxepin-5-ol. The mother liquor is cooled overnight and the formed solid removed by filtration. The resulting mother liquor is evaporated to dryness to give 20 g of cis-4-acetamido-7-methoxy-2,3,4,5-tetrahydrobenzoxepin-5-ol.

Separately, reflux 20 g of either of the so-obtained cis or trans acetamido alcohol, with 60 g of 50% aqueous sodium hydroxide and 150 ml of ethanol under argon for 5 hours. After cooling, each mixture is concentrated in vacuo and the residues poured into cold water (500 ml). On standing overnight, trans-4-amino-7-methoxy-2,3,4,5-tetrahydrobenzoxepin-5-ol precipitates. In the case of the cis compound the cold water solution is extracted with ethyl acetate (5×500 ml) followed by brine-washing, drying (MgSO$_4$) filtration, and evaporation of the combined extracts to yield the cis-4-amino-7-methoxy-2,3,4,5-tetrahydrobenzoxepin-5-ol.

A solution of 17 g of trans-4-amino-7-methoxy-2,3,4,5-tetrahydro-1-benzoxepin-5-ol dissolved in 700 ml of hydrocarbon-stabilized chloroform was treated with 16 ml of triethylamine at room temperature and 10 g of chloroacetyl chloride dissolved in 80 ml of chloroform was slowly added thereto. The reaction mixture was allowed to stand at room temperature for 24 hours and the solid removed by filtration and washed with chloroform. The filtrate was washed twice with dilute hydrochloric acid solution, followed by a wash with water and dried over anhydrous magnesium sulfate. The filtrate was evaporated to dryness and triturated with ether to yield 18.8 g of trans-2-chloro-N-(2,3,4,5-tetrahydro-5-hydroxy-7-methoxy-1-benzoxepin-4-yl)acetamide.

A solution of 18 g of this acetamide dissolved in 750 ml of isopropanol is treated with 9.5 ml of a 50% aqueous solution of sodium hydroxide. The mixture was stirred at room temperature overnight, concentrated in vacuo and diluted with approximately 1 liter of water. The insoluble trans-4a,5,6,11b-tetrahydro-10-methoxy-2H-[1]benzoxepino[5,4-b]-1,4-oxazine-3(4H)-one, 13 g, was removed by filtration and dried. To a mixture of 3 g of lithium aluminum hydride in 500 ml of tetrahydrofuran is slowly added 12 g of the 1,4-oxazine-3(4H)-one above. The reaction mixture is refluxed for a period of 5 hours, cooled in an ice bath and treated with 13 ml of an aqueous 10% sodium hydroxide solution to decompose any excess hydride present. The mixture is stirred overnight, filtered and the filtrate concentrated in vacuo. The residue is dissolved in ether and treated with ethereal hydrogen chloride. The precipitated salt is filtered and recrystallized from methanol/acetonitrile to yield 10.8 grams of the title compound having a m.p. of 260°–262° C.

Following essentially the same procedure, but substituting trans-4-amino-9-methoxy-2,3,4,5-tetrahydro-1-benzoxepin-5-ol and trans-4-amino-8-methoxy-2,3,4,5-tetrahydro-1-benzoxepin-5-ol for the trans-4-amino-10-methoxy-2,3,4,5-tetrahydro-1-benzoxepin-5-ol above, results in the formation of trans-3,4,4a,5,6,11b-hexahydro-8-methoxy-2H-[1]benzoxepino[5,4-b]-1,4-oxazine hydrochloride, having a mp. of 205°–207° C., and trans-3,4,4a,5,6,11b-hexahydro-9-methoxy-2H-[1]benzoxepino[5,4-b]-1,4-oxazine hydrochloride, having a mp. of 230°–232° C.

EXAMPLE 2

Trans-3,4,4a,5,6,11b-Hexahydro-2H-[1]benzoxepino-[5,4-b]-1,4-oxazine Hydrochloride To a solution of 8.07 g of trans-4-amino-2,3,4,5-tetrahydro-1-benzoxepin-5-ol and 9 ml of triethylamine in 400 ml of chloroform is slowly added a solution of 5.58 g of chloroacetyl chloride in 50 ml of chloroform. The mixture is permitted to stand overnight at room temperature, washed with diulte hydrochloric acid solution and filtered through a bed of magnesium sulfate. Evaporation of the filtrate and a recrystallization of the residue from toluene yielded 8.43 g of trans-2'-chloro-N-(2,3,4,5-tetrahydro-5-hydroxy-1-benzoxepin-4-yl)acetamide having a mp. of 141°–144° C.

A solution of 8.3 g of the above amide dissolved in 460 ml of isopropanol is treated with 7.2 g of a 50% aqueous sodium hydroxide solution and the mixture stirred overnight at room temperature. The solvent is concentrated and diluted with water. The insoluble material which forms is removed by filtration and recrystallized from acetonitrile to yield 4.31 g of trans-4a,5,6,11b-tetrahydro-2H-[1]benzoxepino[5,4-b]-1,4-oxazine-3(4H)-one having a mp. of 246°–248° C.

To a suspension of 1.5 g of lithium aluminum hydride in 100 ml of tetrahydrofuran is added, portionwise, 4.18 g of trans-4a,5,6,11b-tetrahydro-2H-[1]benzoxepino[5,4-b]-1,4-oxazine-3(4H)-one. The mixture is refluxed for five hours, cooled in ice and excess hydride decomposed by the addition of 6 ml of 10% sodium hydroxide solution. The resulting mixture is stirred overnight, the solids removed by filtration and the solvent removed by evaporation. The residue is dissolved in ether and treated with ethereal hydrogen chloride. The title compound which precipitates is recrystallized from a methanol/acetonitrile solution to yield 2.69 g of material having a mp. of 259°–260° C.

EXAMPLE 3

Trans-3,4,4a,5,6,11b-Hexahydro-9-ethoxy-N,N-dimethyl-2H-[1]benzoxepino[5,4-b]-1,4-oxazine-4-ethanamine Maleate A solution of 1.21 g of trans-3,4,4a,5,6,11b-hexahydro-9-ethoxy-2H-[1]benzoxepino[5,4-b]-1,4-oxazine hydrochloride, prepared via an analogous procedure to the preceding Example, and 1.65 ml of triethylamine in 25 ml of methylene chloride is treated dropwise with a solution of 0.70 ml of chloroacetyl chloride dissolved in 10 ml of methylene chloride. The reaction mixture is stirred overnight at room temperature, washed with a dilute solution of hydrochloric acid, followed by a water wash, a wash of dilute sodium hydroxide solution and finally by a wash of a saturated solution of sodium chloride. The reaction mixture is dried over anhydrous magnesium sulfate and evaporated to dryness to obtain 1.44 g of trans-N-chloroacetyl-3,4,4a,5,6,11b-hexahydro-9-ethoxy-2H-[1]benzoxepino[5,4-b]-1,4-oxazine.

The N-chloroacetyl derivative above is dissolved in 50 ml of ethanol containing 1.5 grams of dimethylamine and the solution refluxed for approximately 4 hours. The reaction mixture is evaporated to dryness and the residue is taken up with ether. The ether solution is washed with water, followed by a saturated, aqueous brine solution and is dried over anhydrous magnesium sulfate. Treatment of the dried solution with ethereal hydrogen chloride results in the preparation of the N-dimethylaminoacetyl derivative as the hydrochloride salt.

To a stirred suspension of 1.0 g of lithium aluminum hydride in 50 ml of tetrahydrofuran is added the above hydrochloride salt of the N-dimethylaminoacetyl derivative in small portions. The mixture is refluxed for 2 hours under an inert atmosphere of argon, cooled in an ice bath, and cautiously decomposed by the addition of 1.5 ml of water. The mixture is stirred overnight, filtered and the filtrate is evaporated to dryness. The residue is dissolved in ether and treated with a solution of maleic acid in ether to precipitate the title compound as the maleate salt.

Following essentially the same procedure but substituting trans-3,4,4a,5,6,11b-hexahydro-9,10-methylenedioxy-2H-[1]benzoxepino[5,4-b]-1,4-oxazine hydrochloride for the trans-3,4,4a,5,6,11b-hexahydro-9-ethoxy-2H-[1]benzoxepino[5,4-b]-1,4-oxazine hydrochloride above results in the formation of trans-3,4,4a,5,6,11b-hexahydro-9,10-methylenedioxy-N,N-dimethyl-2H-[1]benzoxepino[5,4-b]-1,4-oxazine-4-ethanamine maleate.

EXAMPLE 4

Trans-4-Ethyl-3,4,4a,5,6,11b-hexahydro-10-hydroxy-2H-[1]benzoxepino[5,4-b]-1,4-oxazine Hydrochloride A mixture of 3.47 g of trans-10-phenylmethoxy-3,4,4a,5,6,11b-hexahydro-2H-[1]benzoxepino[5,4-b]-1,4-oxazine hydrochloride, 50 ml of triethylamine and 25 ml of methylene chloride is cooled in ice and 1.0 ml of acetyl chloride dissolved in 25 ml of methylene chloride is added dropwise thereto. The solution is stirred overnight at room temperature, washed with a dilute hydrochloric acid solution and dried over anhydrous magnesium sulfate. The drying agent is removed via filtration and the filtrate evaporated to yield trans-4-acetyl-10-phenylmethoxy-3,4,4a,5,6,11b-hexahydro-2H-[1]benzoxepino[5,4-b]-1,4-oxazine as an oil.

The above 4-acetyl derivative is dissolved in 25 ml of tetrahydrofuran and added dropwise to an ice-cooled suspension of 1.0 g of lithium aluminum hydride in 50 ml of tetrahydrofuran. The mixture is refluxed for approximately 4 hours, cooled in ice and cautiously decomposed by means of 3.5 ml of a 10% sodium hydroxide solution. The reaction mixture is stirred overnight at room temperature, filtered and the filtrate evaporated to dryness in vacuo. The residue is dissolved in ether and treated with an ethereal hydrogen chloride solution to precipitate the trans-4-ethyl-10-phenylmethoxy-3,4,4a,5,6,11b-hexahydro-2H-[1]benzoxepino[5,4-b]-1,4-oxazine hydrochloride.

The 4-ethyl hydrochloride salt is dissolved in 50 ml of ethanol, shaken with hydrogen gas in a Parr shaker at 60 psi in the presence of 0.2 g of 10% palladium/charcoal until hydrogen uptake ceases. The catalyst is filtered, and the filtrate evaporated to dryness. The residue is triturated with ethyl acetate to yield the desired trans-4-ethyl-3,4,4a,5,6,11b-hexahydro-10-hydroxy-2H-[1]benzoxepino[5,4-b]-1,4-oxazine as the hydrochloride salt.

EXAMPLE 5

Trans-3,4,4a,5,6,11b-Hexahydro-10-methoxy-4-methyl-2H-[1]benzoxepino[5,4-b]-1,4-oxazine Maleate A mixture of trans-3,4,4a,5,6,11b-hexahydro-10-methoxy-2H-[1]benzoxepino[5,4-b]-1,4-oxazine, 3.0 ml of triethylamine and 25 ml of methylene chloride is stirred and a solution of 1.0 ml of ethyl chloroformate dissolved in 25 ml of methylene chloride is added dropwise thereto. The mixture is stirred overnight, washed with a dilute hydrochloric acid solution, followed by a saturated sodium chloride solution wash, and dried over magnesium sulfate. The solvent is evaporated and the residue is dissolved in 25 ml of tetrahydrofuran.

This solution is added dropwise to a suspension of 1.0 g of lithium aluminum hydride in 50 ml of tetrahydrofuran. The resulting mixture is refluxed for 6 hours, cooled in an ice bath and excess hydride is decomposed via the cautious addition of 4.0 ml of 10% aqueous solution of sodium hydroxide. The mixture is stirred overnight, filtered and the filtrate evaporated to dryness. The residue is dissolved in ether, treated with an ethereal solution of maleic acid to form the maleate salt. Recrystallization of this salt from a methanol/ethyl acetate mixture provides 1.97 g of the desired title compound.

Following essentially the same procedure but substituting trans-3,4,4a,5,6,11b-hexahydro-8-hydroxy-2H-[1]benzoxepino[5,4-b]-1,4-oxazine and trans-3,4,4a,5,6,11b-hexahydro-8,9-methylenedioxy-2H-[1]benzoxepino[5,4-b]-1,4-oxazine for the starting material above results in the formation of trans-3,4,4a,5,6,11b-hexahydro-8-hydroxy-4-methyl-2H-[1]benzoxepino[5,4-b]-1,4-oxazine maleate and trans-3,4,4a,5,6,11b-hexahydro-8,9-methylenedioxy-4-methyl-2H-[1]benzoxepino[5,4-b]-1,4-oxazine maleate, respectively.

Quite obviously, by starting with the cis-isomeric forms of the compounds of the foregoing examples and by following the same procedures of these examples there are produced the corresponding cis-isomers of the foregoing final compounds.

EXAMPLE 6

Substituted 3,4,4a,5,6,11b-Hexahydro-2H-[1]benzoxepino[5,4-b]-1,4-oxazines

Following essentially the same procedure as described in Example 2, but substituting the following trans-4-amino-2,3,4,5-tetrahydro-1-benzoxepin-5-ols results in the following products shown below.

| Reactants | Product | mp. |
|---|---|---|
| trans-4-amino-7-chloro-tetrahydro-1-benzoxepin-5-ol | trans-10-chloro-3,4,4a,-5,6,11b-hexahydro-2H—[1]-benzoxepino[5,4-b]-1,4-oxazine hydrochloride | 283–284° C. (dec.) |
| trans-4-amino-7-fluoro-2,3,4,5-tetrahydro-1-benzoxepin-5-ol | trans-10-fluoro-3,4,4a,-5,6,11b-hexahydro-2H—[1]-benzoxepino[5,4-b]-1,4-oxazine hydrochloride | 245–250° C. (dec.) |

-continued

| Reactants | Product | mp. |
|---|---|---|
| trans-4-amino-8-chloro-2,3,4,5-tetrahydro-1-benzoxepin-5-ol | trans-9-chloro-3,4,4a,-5,6,11b-hexahydro-2H—[1]-benzoxepino[5,4-b]-1,4-oxazine hydrochloride | 296–298° C. (dec.) |
| trans-4-amino-7-(t-butyl)-2,3,4,5-tetrahydro-1-benzoxepin-5-ol | trans-10-(t-butyl)-3,4,-4a,5,6,11b-hexahydro-2H—[1]benzoxepino[5,4-b]-1,4-oxazine hydrochloride | 293–297° C. (dec.) |
| trans-4-amino-7-methyl-2,3,4,5-tetrahydro-1-benzoxepin-5-ol | trans-10-methyl-3,4,4a,-5,6,11b-hexahydro-2H—[1]-benzoxepino[5,4-b]-1,4-oxazine hydrochloride | 302–303° C. (dec.) |

EXAMPLE 7

Trans-3,4,4a,5,6,11b-Hexahydro-4-methyl-2H-[1]benzoxepino[5,4-b]-1,4-oxazine Maleate A mixture of trans-3,4,4a,5,6,11b-hexahydro-2H-[1]benzoxepino[5,4-b]-1,4-oxazine (prepared as described in Example 2), 3.0 ml of triethylamine and 25 ml of methylene chloride is stirred and a solution of 1.0 ml of ethyl chloroformate dissolved in 25 ml of methylene chloride is added dropwise thereto. The mixture is stirred overnight, washed with a dilute hydrochloric acid solution, followed by a saturated sodium chloride wash, and dried over magnesium sulfate. The solvent is evaporated and the residue is dissolved in 25 ml of tetrahydrofuran.

This solution is added dropwise to a suspension of 1.0 g of lithium aluminum hydride in 50 ml of tetrahydrofuran. The resulting mixture is refluxed for 6 hours, cooled in an ice bath, and excess hydride is decomposed via the cautious addition of 4.0 ml of a 10% aqueous solution of sodium hydroxide. The mixture is stirred overnight, filtered, and the filtrate evaporated to dryness. The residue is dissolved in ether and treated with an ethereal solutin of maleic acid to form the maleate salt. Recrystallization of this salt from a methanol/ethyl acetate mixture yields the compound, trans-3,4,4a,5,6,11b-hexahydro-4-methyl-2H-[1]benzoxepino[5,4-b]-1,4-oxazine maleate having a mp. of 153°–154° C.

Following essentially the same procedure but substituting trans-10-chloro-3,4,4a,5,6,11b-hexahydro-2H-[1]benzoxepino[5,4-b]-1,4-oxazine for the trans-3,4,4a,5,6,11b-hexahydro-2H-[1]benzoxepino[5,4-b]-1,4-oxazine above, results in the formation of trans-10-chloro-3,4,4a,5,6,11b-hexahydro-4-methyl-2H-[1]benzoxepino[5,4-b]-1,4-oxazine maleate having a mp. 142°–143° C.

In a similar way, substituting trans-10-fluoro-3,4,4a,5,6,11b-hexahydro-2H-[1]benzoxepino[5,4-b]-1,4-oxazine for the trans-3,4,4a,5,6,11b-hexahydro-2H-[1]benzoxepino[5,4-b]-1,4-oxazine above and using hydrogen chloride instead of maleic acid, results in the formation of trans-10-fluoro-3,4,4a,5,6,11b-hexahydro-4-methyl-2H-[1]benzoxepino[5,4-b]-1,4-oxazine hydrochloride having a mp. of 244°–245° C.

EXAMPLE 8

Trans-3,4,4a,5,6,11b-Hexahydro-N,N-dimethyl-2H-[1]benzoxepino[5,4-b]-1,4-oxazine-4-ethanamine Maleate A solution of 1.21 g of trans-3,4,4a,5,6,11b-hexahydro-2H-[1]benzoxepino[5,4-b]-1,4-oxazine hydrochloride, prepared according to the procedure of Example 2, and 1.65 ml of triethylamine in 25 ml of methylene chloride is treated dropwise with a solution of 0.70 ml of chloroacetyl chloride dissolved in 10 ml of methylene chloride. The reaction mixture is stirred overnight at room temperature, washed with a dilute solution of hydrochloric acid, followed by a water wash, a wash of dilute sodium hydroxide solution and finally by a wash of a saturated solution of sodium chloride. The reaction mixture is dried over anhydrous magnesium sulfate and evaporated to dryness to obtain 1.44 g of trans-N-chloroacetyl-3,4,4a,5,6,11b-hexahydro-2H-[1]-benzoxepino[5,4-b]-1,4-oxazine.

The N-chloroacetyl derivative above is dissolved in 50 ml of ethanol containing 1.5 grams of dimethylamine and the solution refluxed for approximately 4 hours. The reaction mixture is evaporated to dryness and the residue is taken up with ether. The ether solution is washed with water, followed by a saturated, aqueous brine solution and is dried over anhydrous magnesium sulfate. Treatment of the dried solution with ethereal hydrogen chloride results in the preparation of the N-dimethylaminoacetyl derivative as the hydrochloride salt.

To a stirred suspension of 1.0 g of lithium aluminum hydride in 50 ml of tetrahydrofuran is added the above hydrochloride salt of the N-dimethylaminoacetyl derivative in small portions. The mixture is refluxed for 2 hours under an inert atmosphere of argon, cooled in an ice bath, and cautiously decomposed by the addition of 1.5 ml of water. The mixture is stirred overnight, filtered and the filtrate is evaporated to dryness. The residue is dissolved in ether and treated with a solution of maleic acid in ether to form the maleate salt. Recrystallization of this salt from a methanol/ethyl acetate mixture yields the compound, trans-3,4,4a,5,6,11b-hexahydro-N,N-dimethyl-2H-[1]benzoxepino[5,4-b]-1,4-oxazine-4-ethanamine as the maleate salt, having a mp. of 116°–121° C.

EXAMPLE 9

Trans-4-Ethyl-3,4,4a,5,6,11b-hexahydro-2H-[1]benzoxepino[5,4-b]-1,4 -oxazine

To a stirred solution of 2.41 g of trans-3,4,4a,5,6,11b-hexahydro-2H-[1]benzoxepino[5,4-b]-1,4-oxazine, prepared in accordance with Example 2, and 3.5 ml of triethylamine dissolved in 50 ml of methylene chloride is added dropwise a solution of 0.85 ml of acetyl chloride dissolved in 25 ml of methylene chloride. The mixture is stirred overnight, washed with a dilute hydrochloric acid solution and dried over anhydrous magnesium sulfate. The volatiles are removed by evaporation leaving an oil which yields the compound trans-4-acetyl-3,4,4a,5,6,11b-hexahydro-2H-[1]benzoxepino[5,4-b]-1,4-oxazine having a mp. of 97°–98° C.

To 1.38 g of this 4-acetyl derivative dissolved in 15 ml of tetrahydrofuran is added dropwise a suspension of 0.44 g of lithium aluminum hydride in 25 ml of tetrahydrofuran. The reaction mixture is refluxed for a period of about 5 hours, cooled in ice, cautiously decomposed using 1.2 ml of a 10% aqueous sodium hydroxide solution, and stirred overnight. The reaction mixture is filtered and the solvent evaporated in vacuo to an oil which upon vacuum distillation yielded 1.13 g of trans-4-ethyl-3,4,4a,5,6,11b-hexahydro-2H-[1]benzoxepino[5,4-b]-1,4-oxazine as an oil, having a bp. of 110°–115° C./0.1 mm. of Hg.

Following essentially the same procedure but substituting the following acyl chlorides for the acetyl chloride above, results in the following products and/or their salts as shown below.

| Reactant | Product | mp. |
|---|---|---|
| benzoyl chloride | trans-3,4,4a,5,6,11b-hexahydro-4-(phenylmethyl)-2H—[1]benzoxepino[5,4-b]-1,4-oxazine hydrochloride | 244–245° C. |
| propionyl chloride | trans-3,4,4a,5,6,11b-hexahydro-4-propyl-2H—[1]-benzoxepino[5,4-b]-1,4-oxazine 4-methylbenzenesulfonate | 181–185° C. |
| isobutyryl chloride | trans-3,4,4a,5,6,11b-hexahydro-4-(2-methylpropyl)-2H—[1]benzoxepino[5,4-b]-1,4-oxazine 4-methylbenzenesulfonate | 190–193° C. |
| 2-furoyl chloride | trans-4-(2-furanylmethyl)-3,4,4a,5,6,11b-hexahydro-2H—[1]benzoxepino[5,4-b]-1,4-oxazine hydrochloride | 254–265° C. (dec.) |
| methoxyacetyl chloride | trans-3,4,4a,5,6,11b-hexahydro-4-(2-methoxyethyl)-2H—[1]benzoxepino[5,4-b]-1,4-oxazine | 110–115° C./ 0.6 mm (bp) |
| cyclopropanecarboxylic acid chloride | trans-4-cyclopropylmethyl-3,4,4a,5,6,11b-hexahydro-2H—[1]benzoxepino[5,4-b]-1,4-oxazine hydrochloride | 254–256° C. |

When trans-10-fluoro-3,4,4a,5,6,11b-hexahydro-2H-[1]benzoxepino[5,4-b]-1,4-oxazine was reacted with the appropriate acid chloride according to the procedure described in the first paragraph of the present example, the corresponding 4-amide was obtained. The amide was then reduced with lithium aluminum hydride according to the procedure described in the second paragraph and the resulting product was reacted with 4-toluenesulfonic acid to give the corresponding salt. In this way, the following compounds were obtained:

trans-4-Ethyl-10-fluoro-3,4,4a,5,6,11b-hexahydro-2H-[1]benzoxepino[5,4-b]-1,4-oxazine 4-toluenesulfonate melting at about 163°–166° C.

trans-10-Fluoro-4-propyl-3,4,4a,5,6,11b-hexahydro-2H-[1]benzoxepino[5,4-b]-1,4-oxazine 4-toluenesulfonate melting at about 200°–202° C.

EXAMPLE 10

Trans-10-Fluoro-4-isopropyl-3,4,4a,5,6,11b-hexahydro-2H-[1]benzoxepino[5,4-b]-1,4-oxazine Methanesulfonate A mixture of 6.7 grams of trans-4-amino-7-fluoro-2,3,4,5-tetrahydro-1-benzoxepin-5-ol, 10 ml of acetone and 50 ml of 2,2-dimethoxypropane was refluxed for 2 hours. The solvent was evaporated from the reaction mixture and the residue was subjected to Kuelrohr distillation at 85°–90° C./0.3 mm to give the desired oxazolidine product.

A solution was prepared from 7.0 g of the product obtained in the preceding paragraph and 75 ml of tetrahydrofuran and this was added dropwise to 2.0 g of lithium aluminum hydride in 100 ml of tetrahydrofuran with cooling in an ice bath. The reaction mixture was then refluxed for 10 hours; 1.0 gram of lithium aluminum hydride was added and refluxing was resumed for an additional 4 hours. The reaction mixture was then decomposed by the addition of 6 ml of 10% aqueous sodium hydroxide solution and it was stirred for 16 hours. The mixture was filtered to remove some solids and the solvent was evaporated from the filtrate to leave a residual oil.

The crude oil obtained in the preceding paragraph was dissolved in 100 ml of dichloromethane and 4.0 m of triethylamine was added. The mixture was cooled in ice and a solution of 3.2 g of chloroacetyl chloride in 25 ml of dichloromethane was added dropwise. The mixture was stirred for 40 minutes at which time chromatography showed that no starting material was present. The mixture was washed with dilute hydrochloric acid and the solvent was evaporated to leave a residual oil. This oil was dissolved in 125 ml of 2-propanol, 7.5 g of 50% aqueous sodium hydroxide solution was added and the mixture was stirred for 15 minutes. Solids formed soon after the sodium hydroxide was added. The solvent was then evaporated and the residue was diluted with water to give a gummy solid. The resulting mixture was allowed to stand for 16 hours and the solids were separated by filtration and washed with water. The solid was recrystallized from hexane to give trans-4a,5,6,11b-tetrahydro-4-isopropyl-10-fluoro-2H-[1]benzoxepino[5,4-b]-1,4-oxazin-3(4H)-one melting at about 127°–143° C.

To a suspension of 2.1 g of lithium aluminum hydride in 200 ml of tetrahydrofuran was added 6.06 g of trans-4a,5,6,11b-tetrahydro-4-isopropyl-10-fluoro-2H-[1]benzoxepino[5,4-b]-1,4-oxazin-3(4H)-one in portions and the mixture was then refluxed for about one hour. The mixture was then cooled in ice, decomposed by the addition of 6 ml of 10% aqueous sodium hydroxide solution, and stirred for 16 hours. The solids present in the reaction mixture were separated by filtration and washed with water and the solvent was evaporated from the filtrate to leave a residual oil. The oil was dissolved in ether and a solution of methanesulfonic acid in ether was added until no more cloudiness occurred on addition. The solid was then separated by filtration and triturated in ether to give a tacky solid. This solid was recrystallized from a mixture of methanol and ethyl acetate to give trans-10-fluoro-4-isopropyl-3,4,4a,5,6,11b-hexahydro-2H-[1]benzoxepino[5,4-b]-1,4-oxazine methanesulfonate melting at about 163°–165° C.

EXAMPLE 11

Cis and Trans-4-Amino-2,3,4,5-tetrahydrobenzoxepin-5-ol

A stirred suspension of 43.84 g (0.2M) of 4-acetamido-3,4-dihydrobenzoxepin-5(2H)-one in 60 ml of ethanol was cooled in ice and 10 g of sodium borohydride was added portionwise. After five hours the solvent was removed and the residue dissolved in 800 ml of water. Extraction with $CHCl_3$ gave a mixture of cis and trans-4-acetamido-2,3,4,5-tetrahydrobenzoxepin-5-ol as an oil.

A mixture of the above oil (10.76 g), 25 g of 50% sodium hydroxide and 50 ml of ethanol was refluxed for five hours, cooled and diluted to 400 ml with water. On standing overnight, trans-4-amino-2,3,4,5-tetrahydrobenzoxepin-5-ol precipitated, mp. 144°–146° C. An analytical sample was recrystallized from toluene, mp. 146°–148° C.

Concentration of the filtrate gave crude cis-4-amino-2,3,4,5-tetrahydrobenzoxepin-5-ol. Several recrystallization from ethyl acetate gave the pure cis-amino alcohol, mp. 136°–138° C.

EXAMPLE 12

Cis-4a,5,6,11b-Tetrahydro-2H-[1]benzoxepino[5,4b]-1,4-oxazine-3(4H)-one

A solution of 0.1M of cis-4-amino-2,3,4,5-tetrahydrobenzoxepin-5-ol and 0.11M of triethylamine in 200 ml of methylene chloride was cooled in ice and 0.1M of chloroacetyl chloride in 50 ml of methylene chloride was added dropwise. After stirring overnight at room temperature, the solution was extracted with dilute hydrochloric acid and the solvent evaporated. The residue was stirred with 250 ml of isopropanol and sodium hydroxide (2 equivalents as a 50% aqueous solution) was added. The mixture was stirred overnight, concentrated and diluted with water to give the title product. An analytical sample recrystallized from ethyl acetate had mp. 156°-164° C.

EXAMPLE 13

Cis-3,4,4a,5,6,11b-Hexahydro-2H-[1]benzoxepino[5,4-b]-1,4-oxazine maleate

Cis-4a,5,6,11b-tetrahydro-2H-[1]benzoxepino[5,4-b]-1,4-oxazine-3(4H)-one (0.01M) was added via a solution funnel to a suspension of 0.005M lithium aluminum hydride in 100 ml of dry tetrahydrofuran. The mixture was refluxed for five hours, cooled in ice and decomposed with 15% NaOH. After stirring overnight the mixture was filtered and the solvent removed from the filtrate. The residue was dissolved in ether and treated with a solution of maleic acid in ether to give the title compound. An analytical sample was recrystallized from ethyl acetate, mp. 197°-198° C. (dec.).

EXAMPLE 14

Cis-4-Ethyl-3,4,4a,5,6,11b-Hexahydro-2H-[1]benzoxepino[5,4-b]-1,4-oxazine

A solution of 0.01M of cis-3,4,4a,5,6,11b-hexahydro-2H-[1]benzoxepino[5,4-b]-1,4-oxazine and 0.011M of triethylamine in 25 ml of methylene chloride was cooled in ice and treated dropwise with 0.01M of acetyl chloride in 10 ml of methylene chloride. After stirring at room temperature overnight, the solution was extracted with dilute hydrochloric acid and dried over magnesium sulfate. Evaporation of the solvent left an oil which was dissolved in 10 ml of dry tetrahydrofuran and this solution added dropwise to a suspension of 0.01M of lithium aluminum hydride in 25 ml of tetrahydrofuran. After refluxing five hours, the mixture was cooled in ice and decomposed with 15% sodium hydroxide. After stirring overnight, the solids were filtered and the solvent removed from the filtrate. Kugelrohr distillation of the residue at 110°-116° C./0.2 mm gave the title compound as an oil.

Similarly, by using the cis-isomeric forms of the starting compounds of the foregoing examples and by following the same procedures of those examples, there are obtained the corresponding cis-isomers of the foregoing final compounds.

The compounds of this invention diminish skeletal muscle tone as demonstrated by their antagonism to the so-called morphine-induced Straub tail, K. O. Ellis and J. F. Carpenter, *Neuropharmacology*, 13, 211-14 (1974). Accordingly, the compounds of this invention possess useful muscle relaxant activity and can be used in treating warm-blooded animals in the same manner as known muscle relaxants such as diazepam or mephenesin with due regard being given to the appropriate adjustment of dosages in accordance with the varying activities of these compounds.

In addition, the compounds of this invention have also been found to be useful for the amelioration of pain in warm-blooded animals as measured by the "writhing syndrome" test for analgesic activity as described by B. A. Whittle, *Brit. J. Pharmacol.*, 22, 2246 (1964).

In their end-use applications, either as muscle relaxants or as analgesic agents, the compounds most preferably are utilized in their trans isomeric form, although it is not essential that the administration of the preferred form be such that it be free of any of the cis form.

The term warm-blooded animals as used herein encompasses such species as mice, rats, guinea pigs, rabbits, ferrets, cats, dogs, cows, horses and primates including man.

The administration of these compounds can be carried out either via a parenteral route, such as by intravenous, intramuscular or intraperitoneal injection. Alternatively, the compounds disclosed herein can be introduced into the gastrointestinal tract via oral administration, there to be absorbed into the blood stream. Alternatively, these compounds can be introduced to mammals in need thereof via intratracheal administration, such as by inhalation of a solution of the drug in the form of a spray.

An effective muscle relaxant or analgesic amount is that amount of drug substance which is sufficient to diminish skeletal muscle tone or effect an analgesic response in patients in need thereof. The particular amount of compound employed will vary widely depending upon various factors such as size, type, sex and age of the mammal to be treated, in addition to the mode and frequency of administration, the compound utilized or the particular pharmaceutically acceptable salt employed as well as the degree of hypertension to be treated. In particular instances, the dosage to be administered can be determined via conventional range finding techniques, as for example, by monitoring the reduction in blood pressure at various dose levels.

The compounds herein described can be administered at dosages ranging from about 3 mg to about 3000 mg of a 2H-[1]benzoxepino[5,4-b]-1,4-oxazine derivative, which can be administered from one to four times daily. More particularly, oral dosages of from about 1 to about 30 milligrams per kilogram of animal body weight can be employed. Slightly lower parenteral dosages of from about 0.1 mg to about 10 milligrams per kilogram of animal body weight can be favorably employed.

It is generally desirable to administer the compounds of this invention in dosage unit form. A unit dosage may contain from about 1 to 700 mg of active ingredient, preferably from 5 to 500 mg of active ingredient, and can be taken one or more times per day. Dosage units suitable for oral administration include tablets, capsules, lozenges, elixirs, syrups and the like.

The active compound can be formulated via conventional procedures or as a timed release capable or tablet formulations using techniques well known to those skilled in the art. Where rapid action is desired, the active ingredients may be formulated as injectable compositions, sprays or aerosols for inhalation therapy.

In the practice of this invention, the active ingredient is preferably formulated as compositions comprising from about 5% to about 90% by weight of the particular 2H-[1]benzoxepino[5,4-b]-1,4-oxazine, or a pharmaceutically acceptable salt thereof sought to be administered, in combination with a pharmaceutical carrier.

The term pharmaceutical carrier refers to those pharmaceutical excipients known to the art which are nontoxic and which are useful in the formulation of pharmaceutical compositions. Such compositions can be prepared via techniques known to those skilled in the art for the preparation of tablets, capsules, lozenges, troches, suppositories, elixirs, syrups, emulsions, dispersions, wettable and effervescent powders, sterile injectable compositions and solutions for sprays, and can contain suitable excipients known to be useful in the preparation of the particular type of composition desired. Suitable pharmaceutical carriers and formulation techniques are described in standard texts such as *Remington's Pharmaceutical Sciences*, 16th Edition (1980), Mack Publishing Company, Easton, Pa.

The following illustrates the muscle relaxant activity obtained with the compounds of this invention.

ANTAGONISM OF MORPHINE-INDUCED STRAUB TAIL

The characteristic elevation of the mouse tail (Straub tail) following morphine administration is due to a sustained, centrally mediated reflex contraction of the sacrococcygeus dorsalis muscle. Five to ten mice are used in each test, weight (18 to 30 grams) and placed in a Plexiglass observation chamber 2 to 3 minutes prior to injection. Animals are treated with the test compound at log doses, ca. 10 ml/kg, based upon the $ED_{50}$ obtained from the Rotorod test (reduction of motor ability). Fifteen minutes later the desired dose of morphine sulfate, ca. 10 ml/kg, is injected subcutaneously and the mice observed for a period of 30 minutes following morphine administration for the presence or absence of Straub tail (defined as elevation of tail at 90° C. or more).

REDUCTION OF MOTOR ABILITY

Following a method of Kinnard and Carr, *J. Pharmacol. Exp. Therap.*, 121, 354 (1957), groups of 10 mice are preselected for their ability to remain upon a horizontal rotating (15 rpm) rod (rotorod) for 120 seconds. The mice are dosed with the test compound and tested at various times. The percent change in mean time upon the rotorod from the pre-drug control time of 120 seconds is calculated for each dose group. These data are analyzed by computer using a linear regression program to estimate the $ED_{50}$ with 95% confidence limits and slope. The $ED_{50}$ is defined as the dose of compound producing a 50% decrease in mean time on the rotorod.

| Compound | Straub Tail $ED_{50}$ (mg/kg i.p.) | Rotorod $ED_{50}$ (mg/kg i.p.) |
|---|---|---|
| trans-3,4,4a,5,6,11b-hexahydro-2H—[1]benzoxepino[5,4-b]-1,4-oxazine hydrochloride | 1.03 | 23.9 |
| trans-3,4,4a,5,6,11b-hexahydro-4-methyl-2H—[1]benzoxepino[5,4-b]-1,4-oxazine maleate | 2.89 | 12.4 |

The following illustrates the analgesic activity obtained with the compounds of this invention.

Groups of 5 to 10 mice are administered one or more doses of the test compound by the desired route (but not intraperitoneally). At a selected time the mice are administered acetic acid, 0.4 ml (0.25% v/v solution) i.p. Five minutes later, the mice are observed for a period of 15 minutes to determine the appearance of squirming (abdominal writhing), and the number of squirms for each mouse is determined.

Analgesia is considered significant in those mice which do not squirm during the 15 minute observation period. For $ED_{50}$ determination, four or more doses of compound are tested in groups of 10 mice. The following $ED_{50}$'s for analgesic activity were observed and determined.

| Compound | Pretreatment Time (minutes) | $ED_{50}$ (mg/kg) Subcutaneous | $ED_{50}$ (mg/kg) Oral |
|---|---|---|---|
| trans-3,4,4a,5,6,-11b-hexahydro-4-methyl-2H—[1]benzoxepino[5,4-b]-1,4-oxazine maleate | 30 | 4.35 | 42.8 |
| | 60 | 13.8 | 52.2 |
| | 120 | 26.6 [50% @ 256 mg/kg] | — |
| trans-4-ethyl-3,-4,4a,5,6,11b-hexahydro-2H—[1]benzoxepino[5,4-b]-1,4-oxazine | 30 | 1.5 | 6.8 |
| | 60 | 8.8 | — |
| | 120 | >128 | — |

As stated above, some of the compounds of this invention (Formula I) also possess antihypertensive activity and thus are useful in the treatment of patients suffering from high blood pressure.

More specifically the compounds of Formula I which also possess antihypertensive activity are those of the following formula

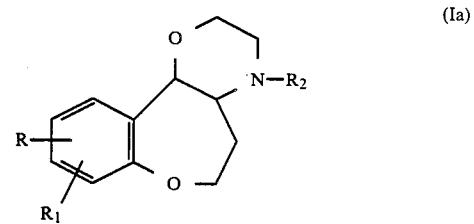

(Ia)

wherein R and $R_1$ are each hydrogen, hydroxy, loweralkyl, halogen, $CF_3$, $NO_2$ or $NH_2$, loweralkoxy, or when taken together are methylenedioxy, $R_2$ is selected from the group consisting of hydrogen, loweralkyl, phenyl(loweralkyl), (loweralkoxy) ($C_{2-4}$ loweralkyl), cyclopropylmethyl, 2-furanylmethyl and $R_3R_4N$-($C_{2-4}$ loweralkyl) wherein $R_3$ and $R_4$ are each hydrogen or loweralkyl; and the pharmaceutical acceptable salts thereof.

In general, in their use as antihypertensive agents, it is found that the compounds may be categorized as $\alpha$-2-receptor antagonists (although their use as antihypertensive agents is not restricted to that mechanism of action). Of particular interest are those compounds wherein either or both of $R_1$ or R are halogen, particularly fluoro and $R_2$ is a $C_{1-3}$ loweralkyl. Preferably the 10-fluoro-4-methyl compound is utilized. The preferred antihypertensive compounds show good potency (i.e. 60% reduction in blood pressure using standard laboratory tests at 3, 10 and 30 mg/kg) and have a prolonged antihypertensive effect.

In practicing this aspect of the invention an effective amount of one or more of the 2H-[1]benzoxepino[5,4-b]-

1,4-oxazines described above are internally administered to a mammal in need thereof. In their end-use application as antihypertensive agents, the compounds most preferably are utilized in their trans isomeric form, although it is not essential that the administration of the preferred form be such that it be free of any of the cis form.

Administration can be carried out either via a parenteral route, such as by intravenous, intramuscular or intraperitoneal injection. Alternatively, the compounds disclosed herein can be introduced into the gastrointestinal tract via oral administration, there to be absorbed into the blood stream. Alternatively, these compounds can be introduced to mammals in need thereof via intratracheal administration, such as by inhalation of a solution of the drug in the form of a spray.

An effective antihypertensive amount is that amount of drug substance which is sufficient to lower or diminish the systemic arterial pressure in patients in need thereof. The particular amount of compound employed will vary widely depending upon various factors such as size, type, sex and age of the mammal to be treated, in addition to the mode and frequency of administration, the compound utilized or the particular pharmaceutically acceptable salt employed as well as the degree of hypertension to be treated. In particular instances, the dosage to be administered can be determined via conventional range finding techniques, as for example, by monitoring the reduction in blood pressure at various dose levels.

The compounds herein described can be administered at dosages ranging from about 3 mg to about 3000 mg of a 2H-[1]benzoxepino[5,4-b]-1,4-oxazine derivative, which can be administered from one to four times daily. More particularly, oral dosages or from about 1 to about 30 milligrams per kilogram of animal body weight can be employed. Slightly lower parenteral dosages of from about 0.1 mg to about 10 milligrams per kilogram of animal body weight can be favorably employed.

The following illustrates the antihypertensive activity obtained with the compounds of this invention.

Spontaneously hypertensive rates (males 250-300 g), obtained from the Charles River Breeding Laboratories, are divided into different treatment groups of 12 rats each. On separate days, one group of 12 rats is given 3, 10 or 30 mg/kg of the test compound, trans-3,4,4a,5,6,11b-hexahydro-10-fluoro-2H-[1]benzoxepino[5,4-b]-1,4-oxazine hydrochloride, by gavage and another group of 12 rats is given water (vehicle, 5 ml/kg).

Systolic arterial blood pressure is recorded from the tail of each rat using an occluding cuff and transducer. Systolic arterial blood pressure is recorded prior and subsequent to the administration of drug or vehicle at 1, 2, 3 and 4 hours post treatment. The results are indicated as follows.

TABLE I

| Dosage of Test Compound (mg/kg) | Change In Systolic Blood Pressure From Control Post Treatment (mm Hg) | | | |
|---|---|---|---|---|
| | 1 Hour | 2 Hours | 3 Hours | 4 Hours |
| 3 | −15* | −20* | −22* | −24* |
| 10 | −52* | −44* | −42* | −45* |
| 30 | −84* | −73* | −73* | −72* |
| Control (water, 5 ml/kg) | 7 | 15 | 10 | 3 |

*Statistically significant ($p < 0.05$)

As can be seen, the test compound produced a dose related decrease in systolic arterial blood pressure that is statistically significant. The duration of the antihypertensive effect is at least 4 hours at the three doses tested.

As noted above, in their end-use application as antihypertensive agents, it is always preferred to utilize the trans form of the compounds of this invention (I), although in such preference it is not absolutely essential that the trans compound be absolutely free from the cis isomer.

What is claimed is:

1. A 3,4,4a,5,6,11b-hexahydro-2H-[1]benzoxepino[5,4-b]-1,4-oxazine having the formula

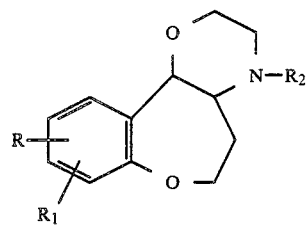

wherein R and $R_1$ are each hydrogen, hydroxy, loweralkoxy, loweralkyl, halogen, —$CF_3$, —$NO_2$ or —$NH_2$, or when taken together are methylenedioxy, $R_2$ is selected from the group consisting of hydrogen, loweralkyl, phenyl(loweralkyl), (loweralkoxy)($C_{2-4}$ loweralkyl), cyclopropylmethyl, 2-furanylmethyl and $R_3R_4N$-($C_{2-4}$ loweralkyl) wherein $R_3$ and $R_4$ are each hydrogen or loweralkyl; and the pharmaceutical acceptable salts thereof.

2. A compound according to claim 1 which has the formula

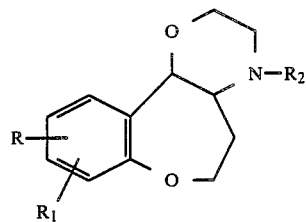

wherein R and $R_1$ are each hydrogen, hydroxy or loweralkoxy; or R and $R_1$ are each loweralkyl, fluoro or chloro or one of them is hydrogen; or R and $R_1$ taken together are methylenedioxy; $R_2$ is selected from the group consisting of hydrogen, loweralkyl, phenyl(loweralkyl), (loweralkoxy) ($C_{2-4}$ loweralkyl), cyclopropylmethyl, 2-furanylmethyl and $R_3R_4N$-($C_{2-4}$ loweralkyl) wherein $R_3$ and $R_4$ are each hydrogen or loweralkyl; and the pharmaceutically acceptable salts thereof.

3. A compound according to claim 2 in which the geometric configuration of the compounds is trans.

4. A compound according to claim 3 which has the formula

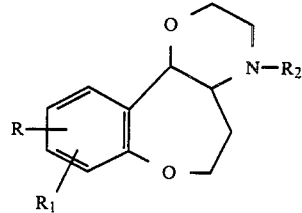

wherein R and R₁ are each hydrogen, loweralkyl, fluoro or chloro; and R₂ is selected from the group consisting of hydrogen, loweralkyl, phenyl(loweralkyl), (loweralkoxy) ($C_{2-4}$ loweralkyl), cyclopropylmethyl, 2-furanylmethyl and $R_3R_4N$-($C_{2-4}$ loweralkyl) wherein R₃ and R₄ are each hydrogen or loweralkyl.

5. A compound according to claim 3 which has the formula

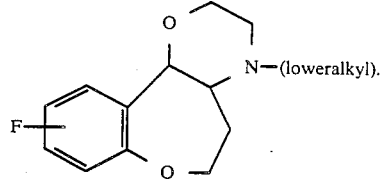

6. A compound according to claim 3 which is trans-10-fluoro-3,4,4a,5,6,11b-hexahydro-4-methyl-2H-[1]benzoxepino[5,4-b]-1,4-oxazine.

7. A compound according to claim 3 which has the formula

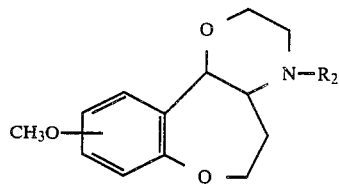

wherein R₂ is hydrogen or loweralkyl.

8. A compound according to claim 3 which is trans-3,4,4a,5,6,11b-hexahydro-10-methoxy-2H-[1]benzoxepino[5,4-b]-1,4-oxazine.

9. A compound according to claim 3 which is trans-3,4,4a,5,6,11b-hexahydro-4-(phenylmethyl)-2H-[1]benzoxepino[5,4-b]-1,4-oxazine.

* * * * *